US011925331B2

(12) United States Patent
Gonsowski

(10) Patent No.: US 11,925,331 B2
(45) Date of Patent: Mar. 12, 2024

(54) CAMERA ACCESSORY DEVICE FOR A LARYNGOSCOPE AND AN ARTIFICIAL INTELLIGENCE AND PATTERN RECOGNITION SYSTEM USING THE COLLECTED IMAGES

(71) Applicant: Charles T. Gonsowski, Klamath Falls, OR (US)

(72) Inventor: Charles T. Gonsowski, Klamath Falls, OR (US)

(*) Notice: Subject to any disclaimer, the term of this patent is extended or adjusted under 35 U.S.C. 154(b) by 0 days.

(21) Appl. No.: 17/352,864

(22) Filed: Jun. 21, 2021

(65) Prior Publication Data
US 2022/0007928 A1 Jan. 13, 2022

Related U.S. Application Data

(60) Provisional application No. 63/156,854, filed on Mar. 4, 2021, provisional application No. 63/051,113, filed on Jul. 13, 2020.

(51) Int. Cl.
A61B 5/05 (2021.01)
A61B 1/00 (2006.01)
(Continued)

(52) U.S. Cl.
CPC ........ A61B 1/2673 (2013.01); A61B 1/00013 (2013.01); A61B 1/00016 (2013.01); A61B 1/267 (2013.01); A61B 5/4842 (2013.01); A61B 5/7246 (2013.01); A61B 5/7267 (2013.01); G06N 3/00 (2013.01); G06N 3/02 (2013.01); G06N 3/08 (2013.01); G06N 3/088 (2013.01); G06N 20/00 (2019.01); G06T 7/0012 (2013.01);
(Continued)

(58) Field of Classification Search
CPC .............. A61B 1/2673; A61B 1/00013; A61B 1/00016; A61B 1/267; A61B 5/4842; A61B 5/7246; A61B 5/7267; A61B 1/00096; A61B 1/0064; A61B 1/00112; A61B 1/00163; G06K 9/00496; G06K 9/00536; G06K 9/46; G06K 9/64; G06K 9/66; G06N 3/00; G06N 3/02; G06N 3/08; G06N 3/088; G06N 20/00; G06T 7/0012; G16H 10/60; G16H 50/20
See application file for complete search history.

(56) References Cited

U.S. PATENT DOCUMENTS 8,187,180 B2  5/2012  Pacey
8,858,425 B2  10/2014 Farr et al.
(Continued)

OTHER PUBLICATIONS

Ren et al. "Automatic Recognition of Laryngoscopic Images Using a Deep-Learning Technique." The Laryngoscope 130(11):E686-E693 (first published Feb. 18, 2020).*

Primary Examiner — Joel F Brutus
(74) Attorney, Agent, or Firm — Bold IP, PLLC; Christopher Mayle

(57) ABSTRACT

A system and method for a laryngoscopic device which incorporates the electronic and imaging elements within the device with advanced functional iterations that incorporate mathematical pattern recognition/predictive modeling as well as parallel computing and supercomputing for data analysis as well as and integrating it with the patient's record and compiling images from multiple scopes in a cloud-based system for an AI platform to use in diagnosis and disease monitoring.

17 Claims, 6 Drawing Sheets

(51) Int. Cl.

| | | |
|---|---|---|
| *A61B 1/267* | (2006.01) | |
| *A61B 5/00* | (2006.01) | |
| *G06N 3/00* | (2023.01) | |
| *G06N 3/02* | (2006.01) | |
| *G06N 3/08* | (2023.01) | |
| *G06N 3/088* | (2023.01) | |
| *G06N 20/00* | (2019.01) | |
| *G06T 7/00* | (2017.01) | |
| *G06V 10/40* | (2022.01) | |
| *G06V 10/75* | (2022.01) | |
| *G06V 30/194* | (2022.01) | |
| *G16H 10/60* | (2018.01) | |
| *G16H 50/20* | (2018.01) | |

(52) U.S. Cl.
CPC .............. *G06V 10/40* (2022.01); *G06V 10/75* (2022.01); *G06V 30/194* (2022.01); *G16H 10/60* (2018.01); *G16H 50/20* (2018.01); *G06F 2218/00* (2023.01); *G06F 2218/12* (2023.01)

(56) References Cited

U.S. PATENT DOCUMENTS

| | | | |
|---|---|---|---|
| 2009/0247833 | A1 | 10/2009 | Tanaka |
| 2010/0261968 | A1* | 10/2010 | Nearman ............... A61B 1/008 600/188 |
| 2013/0237763 | A1* | 9/2013 | Qiu .................. A61M 16/0488 600/188 |
| 2015/0190044 | A1 | 7/2015 | Livnat |
| 2016/0206189 | A1* | 7/2016 | Nearman ............... A61B 1/008 |
| 2018/0168433 | A1 | 6/2018 | Meyer et al. |
| 2018/0353073 | A1* | 12/2018 | Boucher ................. A61B 5/05 |
| 2019/0125457 | A1* | 5/2019 | Parihar .................. A61B 34/10 |
| 2019/0188870 | A1* | 6/2019 | Park .......................... G06T 7/30 |
| 2020/0245960 | A1* | 8/2020 | Richter .................. G16H 50/20 |

* cited by examiner

CAMERA ACCESSORY DEVICE FOR A LARYNGOSCOPE AND AN ARTIFICIAL INTELLIGENCE AND PATTERN RECOGNITION SYSTEM USING THE COLLECTED IMAGES

CROSS REFERENCE TO RELATED APPLICATIONS

This a Non-Provisional application which claims priority to Provisional Application 63/051,113 filed on Jul. 13, 2020 and Provisional Application 63/156,854 filed on Mar. 4, 2021 which are incorporated in their entirety.

FIELD OF DISCLOSURE

The overall field of this invention generally relates to medical imaging. In particular, the invention relates to one or more systems for performing medical imaging that utilizes a laryngoscope with an attached video imaging device, whereby images obtained from the laryngoscope with the attached video imaging device may be used for various purposes including for purposes of referring to the images as a part of a patient's medical record and to study disease progression.

BACKGROUND

Endotracheal intubation is the process of inserting an endotracheal tube (ETT) through an open glottis into the trachea for the purpose of ventilating the lungs. Endotracheal intubation is facilitated with a device called a laryngoscope. A laryngoscope consists of a handle attached to a laryngoscope blade. The laryngoscope blade is placed into the mouth and used to displace the tongue and other pharyngeal structures in order to create a direct visual line of site from the operators eye to the glottis, which is the hole that appears leading into the trachea when the vocal cords move laterally, where the tip of the of the ETT is approximated and then manually advanced through the glottis and into the trachea thus securing the airway and allowing ventilation to occur. The process of using the laryngoscope to provide a direct line of site from the operator's eye to the glottis defines direct laryngoscopy.

Whereas the process of direct laryngoscopy and successful endotracheal intubation most commonly occurs uneventfully, on occasion, certain individual anatomic configurations make directly visualizing the glottis difficult, if not impossible. Hence, a variety of devices have been introduced to circumvent this problem including video laryngoscopy. Video laryngoscopy, in all its permutations, essentially involves attaching a camera to the blade component of the laryngoscope which then feeds back live images of the glottis to some sort of display. In this way, endotracheal intubation can be achieved through indirect visualization.

However, there still exists a need for a laryngoscopic device that not only transmits images wirelessly to a display device, but also provides subsequent iterations incorporating extended adjunctive capabilities currently not available, such as local monitoring of transmitted live video images, remote monitoring of live wirelessly transmitted images, remote cloud storage of high definition digital images, storage of glottic images for individual patient medical records, and compiling a large digital data set to be utilized by Artificial Intelligence (AI) to recognize glottic images and subsequently provide diagnosis, treatment, and data regarding the natural progression of a disease.

DETAILED DESCRIPTION

Figure 1:
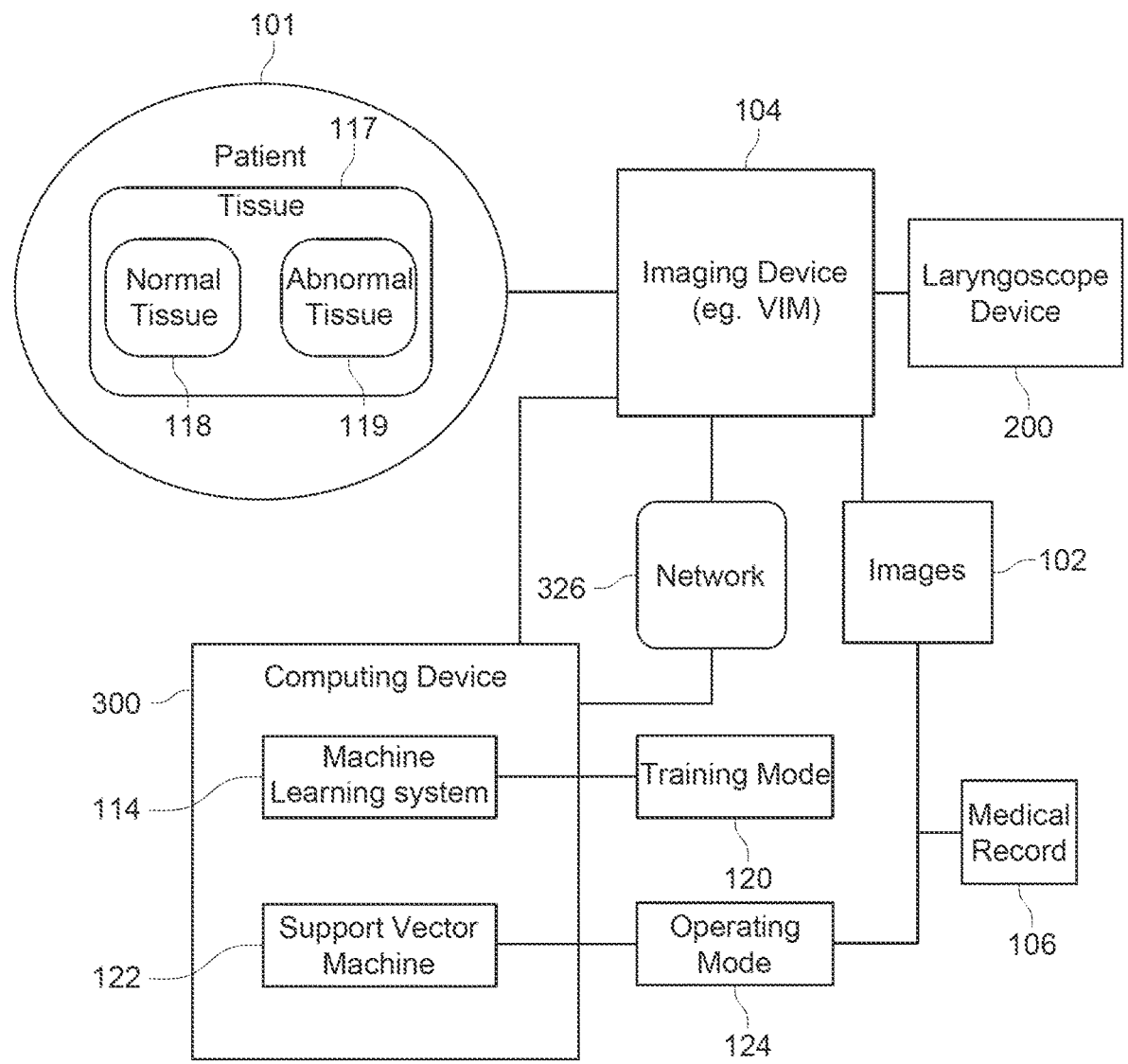
FIG. 1 illustrates a block diagram of exemplary components of a system for imaging and classification of tissue using one or more embodiments of the invention.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

Where reference is made herein to a method comprising two or more defined steps, the defined steps may be carried out in any order or simultaneously (except where the context excludes that possibility), and the method may include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any items, so a "set of items" may indicate the presence of only one item or may indicate more items. Thus, the term "set" may be equivalent to "one or more" as used herein.

The present disclosure recognizes the unsolved need for a laryngoscopic device which incorporates the electronic and imaging elements within the device, including a laryngoscopic imaging device with advanced functional iterations that incorporate mathematical pattern recognition/predictive modeling as well as parallel computing and supercomputing for data analysis. Pattern recognition is the process of recognizing patterns by using machine learning algorithm. Predictive modeling uses technology and statistics to search through massive amounts of data outcomes. One or more embodiments, in addition to providing a video imaging system to aid in intubation, also provide a system of storing the images and integrating it with the patient's record and compiling images from multiple scopes in a cloud-based system for an AI platform to use in diagnosis and disease monitoring. The invention will provide superior convenience, accessibility, affordability, and image quality with a high definition video imaging system to facilitate manual intubation of the trachea during examination. The device will have functional iterations that incorporate extended adjunctive capabilities currently not available with any laryngoscopic imaging device.

One or more embodiments of the invention disclose a method and apparatus comprising an imaging device integrated with machine learning that uses shared data and/or predictive modeling to identify and/or predict abnormal growth or other physical and visually detectable interval changes in images. The system can comprise an imaging module affixed to a laryngoscope and/or bronchoscope integrated with an artificial intelligence (AI) platform, as well as include pattern recognition, and storage to a patient's record.

A system according to one or more embodiments can comprise one or more scopes (i.e. laryngoscope and/or bronchoscope) coupled to a computing device with one or more processors, wherein one or more processors obtain training data from one or more first images, wherein one or more abnormal regions and one or more normal regions are identified. The system may further receive a second image captured at a later time by one or more scopes, and generate one or more abnormalities in the second image if identified using machine learning trained using the training data. One or more of the embodiments of the invention also disclose a method comprising machine learning that uses shared data and/or predictive modeling to train a machine having advanced capabilities adapted with a laryngoscope like device to autonomously perform tracheal intubation.

Cloud and or parallel computing can be used to connect scopes such that the images and other pertinent data can be compiled in a central location to be accessed, shared, and used as training data so that the machine learning learns from the training data to identify the one or more abnormalities in the images during operative stage. A multi-central supercomputing/parallel computing and machine learning apparatus may also be provided.

One or more embodiments of the invention can be applied to the images collected and stored post intubation procedure to identify abnormalities from pattern recognition in the training data. One or more embodiments of the invention can also be implemented in real time during the intubation procedure so the machine trained device can identify abnormal growth using pattern recognition software.

The laryngoscopic video imaging system disclosed herein is intended to provide and not be limited to local monitoring of wirelessly transmitted live video images to a computing device to facilitate the manual intubation of the trachea. Additionally, the largyngoscopic video imaging system disclosed herein is intended to provide, without limitation thereto, remote monitoring of live wirelessly transmitted video images. Additionally, the system as described herein is configured to provide remote cloud storage of high-definition (HD) digital images and storage of glottic images for individual patient medical records. Additionally, the laryngoscopic video imaging system disclosed herein is capable of compiling a large digital image data set from multiple scopes which can be stored in a central database that also utilizes an artificial intelligence/machine learning platform (software).

The data obtained from the imaging system will be used to train a machine to recognize the images of the glottis and the surrounding tissue and will subsequently be very important for recognizing normal and abnormal tissue in the region to efficiently and accurately track disease progression. Thus, artificial intelligence can process the compiled large digital image data set which, in combination with other correlated clinical information, may be used to provide novel medical insights into the diagnosis, treatment, and natural progression of disease.

The video imaging system and integration with AI and pattern recognition of the present disclosure is comprised of two main parts. The first part may include a video imaging accessory to facilitate manual endotracheal intubation. The second part of the video imaging system may include a digital database of HD glottic images that is accessible by a cloud-based storage and AI platform. The first part of the video imaging system noted above is comprised of a disposable detachable housing, a reusable video imaging module (VIM) which is designed to be contained within the detachable housing, and the associated software. The detachable housing attaches/detaches to a preexisting laryngoscope blade and is designed to contain the video imaging module. The video imaging module consists of a HD video imaging element (e.g. camera) and associated electronic hardware to wirelessly send acquired video images to a computing device.

The second part of the video imaging system noted above is comprised of a software program on the computing device which facilitates the wireless transmission of HD digital video images from the VIM to the computing device. The software will receive wireless transmission of digital video images from the VIM for both live display and storage as a part of the personal medical record as well as for subsequent transfer to a cloud-based storage and AI processing platform. The software platform also implements the storage and processing of acquired digital database of HD glottic images transmitted by a second party cloud-based storage and AI platform. The processing would be provided by a cloud-based platform. This cloud-based platform may provide access to as well as storage of HD laryngeal/glottic images that can become a part of an individual's personal medical record.

As discussed above, the VIM may include a wireless transmitter for wirelessly transmitting the output of a camera to a wireless receiver that is coupled to the computing device. A camera may output still images or moving images to the computing device. The video display system may be a video monitor, screen, or another device with a screen such as a smartphone, tablet, or personal computer. The video display system may be associated with an app or software which facilitates the wireless transmission of the video images from the VIM to the video display system. Thus, the video stream from the VIM can be displayed using the app or directly on the video display. The software may allow the live procedure to be viewed on the screen and also save the file to the patient's record. The software application may receive the live images as well as store the images as part of a personal medical record. Preferably, the video images are transferred through the software to a cloud-based storage system.

Routine use of the VIM device with the associated software may produce an increasing number of digital images of the glottic structures. The images may be transferred to a cloud-based storage system which could then be accessible for an Artificial intelligence (AI) platform where the increasing set of data would be used to train a neural network and develop an AI machine learning model on a particular medical task. Such a task may include identifying disease progression by simple comparison of serial images. For example, transfer learning has emerged as a highly popular technique in developing deep learning models. In transfer learning, the neural network is trained in two stages. The first stage may include pretraining, where the network is generally trained on a large-scale benchmark dataset representing a wide diversity of labels/categories. The second stage may include fine-tuning, where the pretrained network is further trained on the specific target task of interest, which may have fewer labeled examples than the pretraining dataset. The pretraining step helps the network learn general features that can be reused on the target task. This kind of two-stage paradigm has become extremely popular in many settings, and particularly so in medical imaging. For training, the machine learning algorithm system will use a set of input images to identify the image properties that, when used, will result in the correct classification of the image and also for predictive modeling, whereby once the system has learned how to classify images, the learned model maybe applied to new images to assist in identifying a disease or disease progression.

In one or more embodiments, the invention discloses a method and apparatus which comprises machine learning that uses shared data and/or predictive modeling to identify and/or predict abnormal growth in images. The system may comprise, without limitation thereto, the VIM device, the VIM software application, AI, and pattern recognition. The system may also comprise one or more imaging devices (e.g. HD camera mounted on a laryngoscope blade) coupled to one or more processors, wherein the one or more processors obtain training data from one or more first images, wherein one or more abnormal regions and one or more normal regions are identified. The system may then receive a second image (e.g., an optical image) captured by one or more of the scopes at a later time than the one or more first images and/or captured using a different imaging technique, and generate, using machine learning trained using the training data, one or more viewable indicators identifying one or more abnormalities in the second image.

Cloud and/or parallel computing can be used to connect scopes so that the scopes can access, share, and learn from the data obtained from different scopes. A multi-central parallel computing and machine learning apparatus can be provided. For example, the scopes can comprise one or more first scopes capturing the one or more first images of one or more patients and a second scope capturing the second image of a different patient. The system can further comprise a cloud and/or supercomputing/parallel computing system wherein the training data obtained from the one or more first images captured in the one or more first scopes is shared so that the machine learning learns from the training data to identify the one or more abnormalities in the second image of the different patient.

The present disclosure also describes the use of AI that will be integrated to improve patient care by speeding up processes and achieving greater accuracy. A patients' electronic medical record (EMR) which will include the glottic images collected and stored in the cloud-based program can be evaluated by machine learning, aiding in the process of diagnosis and treatment of patients and augmenting physicians' capabilities.

One or more embodiments also provide for a visualization platform that may include a video imaging system comprising of a video imaging device and its associated electronic components housed within a laryngoscope handle and utilizing an optical conduit that connects to a laryngoscope blade to assist in intubation. As disclosed herein, a laryngoscope device with a video imaging system is intended to provide and not be limited to local monitoring of wirelessly transmitted live video images to a computing device to facilitate in the manipulation and visualization of soft tissue and airway structures in a patient's airway. Additionally, the laryngoscope device with a video imaging system also provides a platform for taking still images which may be used and stored as part of a patient's medical record. A single device is created that may be used for airway management with a visualization platform rather than providing a visualization attachment that has to be connected to a laryngoscope device wherein the attachment may be disposable or non-disposable. Thus, the disclosed invention will provide superior convenience, accessibility, affordability, and image quality with a high-definition video imaging system to facilitate in the manipulation and visualization of soft tissue and airway structures in a patient's airway.

The video imaging system (as mentioned above) is comprised of the video imaging device and its associated electronic components. In one or more embodiments, the video imaging system may comprise of a HD video imaging element (e.g., camera) and associated electronic hardware, which would be housed in a handle of an airway management tool, to wirelessly send acquired video images to a computing device. The video imaging device may be electrically connected to the associated electronic components in the handle. Alternatively, in one or more embodiments, the video imaging system may comprise of a fiberoptic element that transmits images to the electronic components contained within the handle of the airway management tool.

Turning to FIG. 1, FIG. 1 illustrates a block diagram of a system and method for imaging using machine learning, according to one or more embodiments of the invention. In one or more non-limiting embodiments, a medical video imaging system includes one or more images 102 of tissue regions 117 (e.g. epiglottis, larynx, trachea, etc.) for a patient 101. The system may obtain these images 102 of tissue regions 117 using an imaging device 104. The imaging device 104 may include a camera or other audiovisual device that is connected to (either permanently or removably) to the laryngoscope.

The system may further include a machine learning system 114 wherein one or more images 102 of tissue regions 117 are combined together and used to train machine learning system 114 when the machine learning system 114 is operating in a training mode 120. The system may include a machine learning system 114 wherein data from a medical record 106 which includes and is not limited to medications, vitals, past medical history or other concomitant disease processes, and other correlations between a particular observation with an abnormality can be supported by a reference in the medical record. The system may further include, without limitation, a support vector machine 116. The support vector machine is a supervised learning model that uses classification algorithms for classification. The support vector machine 116 is then used in an operating mode 124 in the classification of tissue 117 into normal tissue 118 and abnormal tissue 119 in the image data. The support vector machine 116 in the operating mode 124 would also make correlations between the images 102 and the medical record 106 to identify patterns in an image associated with a particular element in the medical record. An example would be where a patient with a history of a particular disease or condition taking a certain medication demonstrates a correlation with a particular vascular pattern or other physical quality detectable in the images which may be associated with an increased risk of laryngeal cancer or other disease process or pathology. Machine learning would identify this correlation. Thus, the machine learning system 114 can use machine learning and pattern recognition to identify abnormal growth (i.e. abnormal tissue 119) in images 102 captured by the imaging device 104 and further make correlations with elements found within the medical record 106.

Machine learning technology can be improved by using technologies such as Hidden Markov, Adaptive Boosting (ADABOOST), or other machine learning technologies to obtain more accurate results for the classification of normal and abnormal tissue. The results can be compared by an expert, such as a medical care provider, using the images used in the machine learning system 114 to determine accuracy of the machine classification. Subsequently, the results of the accuracy determination can be used to improve the machine learning technology so that more accurate results for the classification of tissue 117 is achieved.

A logical flow for identifying abnormal regions in an image taken from a patient during a procedure (e.g., endotracheal intubation and/or bronchoscopy) may be represented as obtaining training data from first data or one or more first images (e.g. images 102) wherein one or more normal regions and one or more abnormal regions (e.g. normal tissue 118 and abnormal tissue 119) are identified. The training data can comprise human or AI classifications of the normal and abnormal regions. The training data would also comprise medical records 106 to make correlations between an observed anomaly and references within the medical record. One or more second images and/or data may be captured at a later time. Machine learning may be used to generate one or more viewable indicators identifying one or more normal and/or abnormal regions in the one or more second images. Machine learning would also be used to make correlations between an observed anomaly and relevant data within the medical record 106. The training data can be inputted to, and the machine learning method/system can be implemented on, a machine such as a computing device (discussed in FIG. 3). The machine learning system 114 can be trained using the training data to identify one or more abnormal regions in the second image.

The machine learning system 114 can use pattern recognition or recognize regularities or correlations in data obtained from the first and second images and relevant data within the medical record of a patient. Alternative methods/systems can also be used to discover previously unknown patterns (unsupervised learning), or a combination of supervised and unsupervised learning can be used (semi-supervised learning). The learning method/system can be implemented on one or more processors or computers (e.g. see FIG. 3) connected to the imaging device 104, which may be connected wirelessly or via a wired network connection in one or more non-limiting embodiments.

The learning method/system may be comprised of a support vector machine (SVM) such as support vector machine 122 shown in FIG. 1 The SVM 122 may analyze the training data and recognize patterns or correlations in the training data and subsequently build a model to classify the images (102 in FIG. 1) of tissue as normal or abnormal (118 and 119, respectively).

Figure 2A:
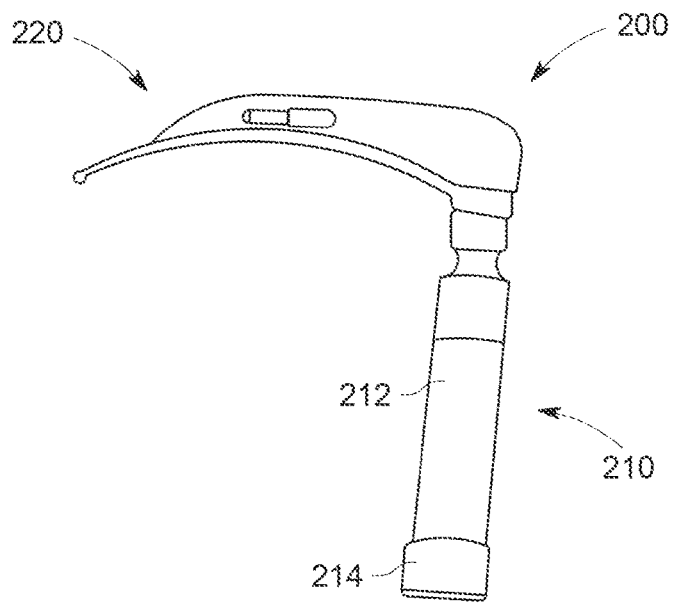
FIG. 2A illustrates a laryngoscope device as an apparatus to which an imaging device may be attached.
Figures 2B, 2C:
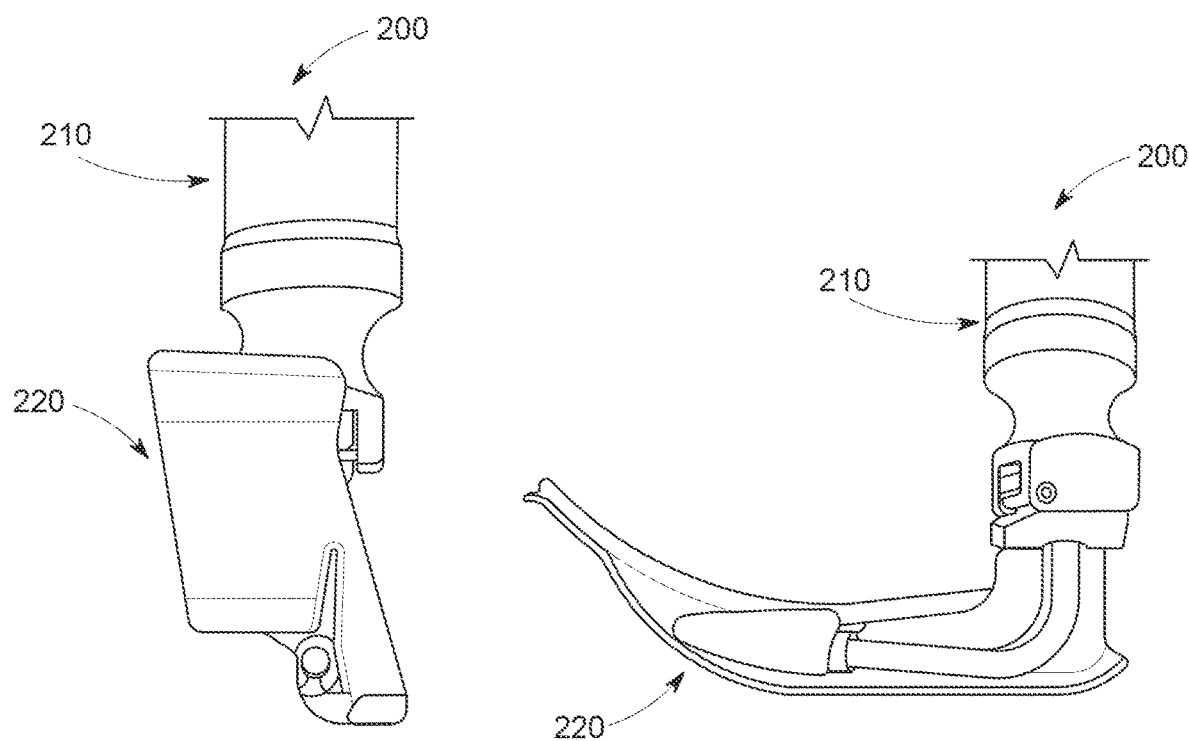
FIG. 2B illustrates a front view of the laryngoscope device as an apparatus to which an imaging device may be attached.
FIG. 2C illustrates a side view of the laryngoscope device as an apparatus to which an imaging device may be attached.

Turning to FIGS. 2A-2C, a laryngoscope device 200 represents an apparatus to which an imaging device (such as the imaging device 104 of FIG. 1) may be coupled to, so as to capture one or more images during an endotracheal intubation. The standard laryngoscope shown in FIG. 2 is a Welch-Allen MAC 3, and is illustrative of a general laryngoscope that may be used by clinicians and is amenable to accommodating and incorporating the presently disclosed video imaging system (not shown). The presently disclosed video imaging system may also be incorporated into and comprise part of a newly designed airway management tool with a fully integrated video imaging system.

Figure 5:
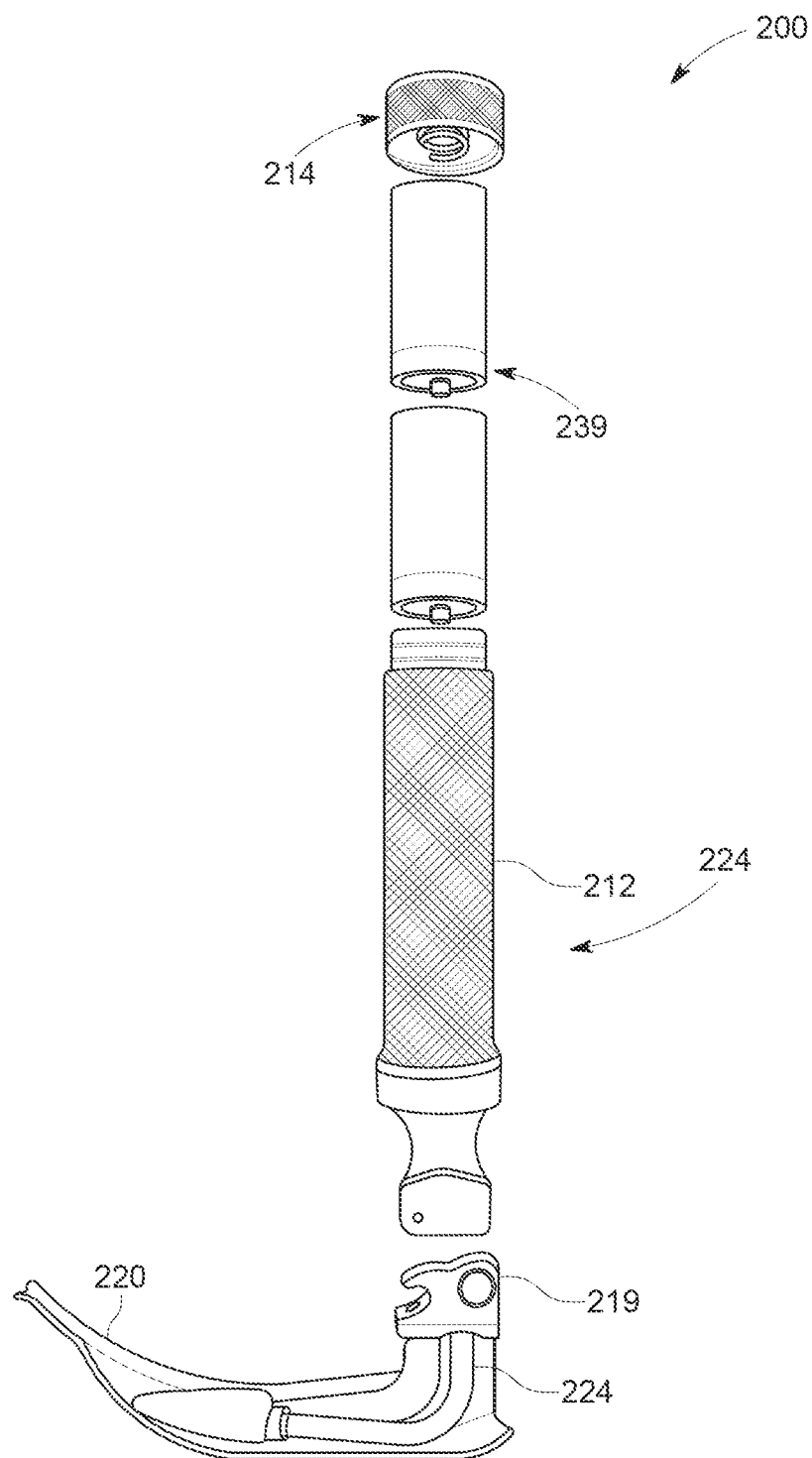
FIG. 5 illustrates a laryngoscope device as an apparatus to which an imaging device may be attached.

In FIG. 5 the laryngoscope device 200 is shown which includes a base unit 210 and a standard laryngoscope blade 220 in a connected position. The base unit 210 includes a handle 212 where a user holds the base unit 210. The base unit 210 may further include a cap 214, which provides access to the inside of the handle 212. The handle 212 is generally hollow and is designed to house a power source, such as batteries 239 and the electrical connection to a light source (not shown) which is provided at a distal end of the laryngoscope blade 110 which transmits the light from the lamp to be directed into the larynx for illuminating the glottis under direct visualization. Handle 212 has a first end and a second end, wherein the first end may have cap 214 which may be removed to access the interior of the handle 212. The second end of handle 212 is connected to a proximal end of the blade 220 of the laryngoscope and secured via a blade base 219.

The laryngoscope blade 220 includes a first end and a second end, wherein the first end attaches to the base unit 210 and the second end is configured to be inserted into the throat of a patient (such as patient 101 in FIG. 1)). FIG. 2A is used to illustrate the basic components of an airway management tool such as the laryngoscope that may be used to incorporate the imaging device (FIG. 1, 104) provided for in this disclosure.

Figure 6:
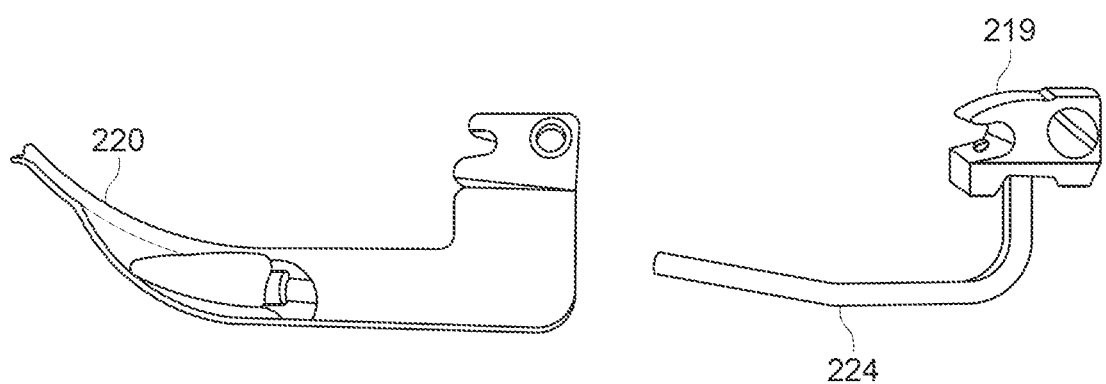
FIG. 6 illustrates a general laryngoscope blade and an optical conduit.

FIG. 6 shows the blade 220 and an optical conduit 224 that fits along a side of the blade 220. The distal end of the blade 220 is positioned and placed into a mouth of a subject whose airway is being accessed. The optical conduit 224 serves the purpose of providing a conduit for the electrical wires that connect the batteries 236 to the light source at the distal end of the laryngoscope. The optical conduit 224 as shown in FIGS. 1 and 2 is usually made of metal to protect the optic system. A distal tip of the optical conduit 224 houses the light source.

The description above is of a general laryngoscope for demonstration purposes only and to enable an understanding of how the presently disclosed video imaging system may be integrated into a standard and generally available laryngoscope, such as the laryngoscope 100 described above.

Various imaging devices (not shown in FIGS. 2A-2C) may be attached to the laryngoscope blade 220. The imaging device (such as the imaging device 104 in FIG. 1) may be included in a housing that contains the respective hardware and software components which will collectively be referred to as a video imaging module (VIM). The housing of the imaging device 104 is designed to contain the video imaging module (VIM). The VIM is comprised of the video imaging elements (such as a camera) and electronic hardware to wirelessly send acquired video and still images to an electronic device (e.g. computing device 300 in FIG. 3). The VIM is designed to be contained within the housing, as discussed above. In one or more non-limiting embodiments, the housing would have attachment means to securely hold the VIM in a predetermined position such that the video camera is directed toward and facing the front side of the laryngoscopic blade 220 so as to provide visualization and acquire images as the user (e.g. a doctor or other medical provider) is inserting the blade 220 into the patient's (such as patient 101 in FIG. 1) throat. The VIM is also intended to be reusable and thus is removable from within the housing. Hardware components may include a microprocessor and a wireless communication chipset. The microprocessor may be utilized for functions including video processing, encoding and streaming and also for still image processing and encoding. The wireless communication chipset may function with 802.11, Bluetooth®, or another wireless communication protocol capable of streaming video. The wireless communication chipset may be integrated into or with the microprocessor chip.

Preferably, the VIM is secured within a reusable housing which is designed to seal the VIM in an enclosed chamber, thereby preserving the sterility of the VIM. The VIM is reusable and thus may be reused by attaching it in a new sterile housing described in this disclosure. The camera is also preferably operably connected to a power source, such as a battery, which is contained in within the VIM. The power source would preferably be rechargeable. Alternatively, the power source may also be contained within the base unit 210. The camera is preferably a high definition (HD) Complementary Metal Oxide Semiconductor (CMOS) camera which uses narrow band frequencies and can switch between these narrow band frequencies. These frequencies include and are not limited to ultraviolet, visible, near-infrared, and infrared. Alternatives may include standard definition (SD) camera and Charged Coupled Device (CCD) cameras.

The camera in the VIM is operably connected to a computing device 300 (e.g. computing device 300 as discussed in FIG. 3) and the captured image is processed using the computing device. The image may be enhanced or manipulated using a software package capable of doing so. In one or more embodiments, a software on the computing device can be used to capture and subsequently display and store the images on the computing device. In one or more embodiments, the image capturing, and processing can be implemented in multiple computing devices and/or using multiple imaging devices (i.e. VIM) wherein each performs one or more steps (e.g. using cloud computing). Results from each of the imaging systems and/or computing devices can be combined to improve identification of an abnormality. Accordingly, one or more embodiments described herein provide for a computer implemented system that can process and display live images, manage and store the image data obtained from the VIM, and combine multiple imaging systems to use in a machine learning system (e.g. machine learning system 114) to subsequently classify normal and abnormal tissue using machine learning/pattern recognition.

In accordance with a non-limiting exemplary embodiment, the housing may be adapted to removably couple to the laryngoscope blade 220. The housing can be quickly attached and detached from the laryngoscope device 200. The housing may be disposable or made of a material that allows the housing to be autoclavable after each use. The housing body would have an attachment means to couple to the laryngoscope blade 220. The housing body would also permit the VIM to be housed and oriented in a predetermined position such that a video camera, which comprises a part of the VIM, is directed toward the second end of the laryngoscope blade 220.

FIG. 2B illustrates a front side of the laryngoscope device 200 with the laryngoscope blade 220 which has a bottom side, a top side, a left side, and a right side. The attachment member of the housing may be adapted to removably fit on the bottom side of the laryngoscope blade 220. In this non-limiting embodiment, the attachment member may be provided as a retaining clip along the length of a top surface of the housing such that the retaining clip may slide over a left side of the laryngoscope blade (when viewing from the front) and securely hold in place till it is removed. The attachment member of the housing may also be adapted to removably fit on the right and the top side along the illuminating optic conduit which is attached to the laryngoscope device 200. FIG. 2C illustrates the right side of the laryngoscope blade 220 with the illuminating optic conduit. Attachment members may also include other means such as and not limited to a clamp.

In one embodiment, the housing may be designed to fit only one type of blade or only blades of a particular geometry. In an alternative embodiment, housing may be designed to fit a variety of blade designs. For example, attachment member may be a receptacle of a shape or cross-section that is designed to fit a variety of blade cross-sections. Similarly, attachment member may be a clamp that is designed to be attached to a variety of blade designs, or in a variety of locations on the blade.

Figure 3:
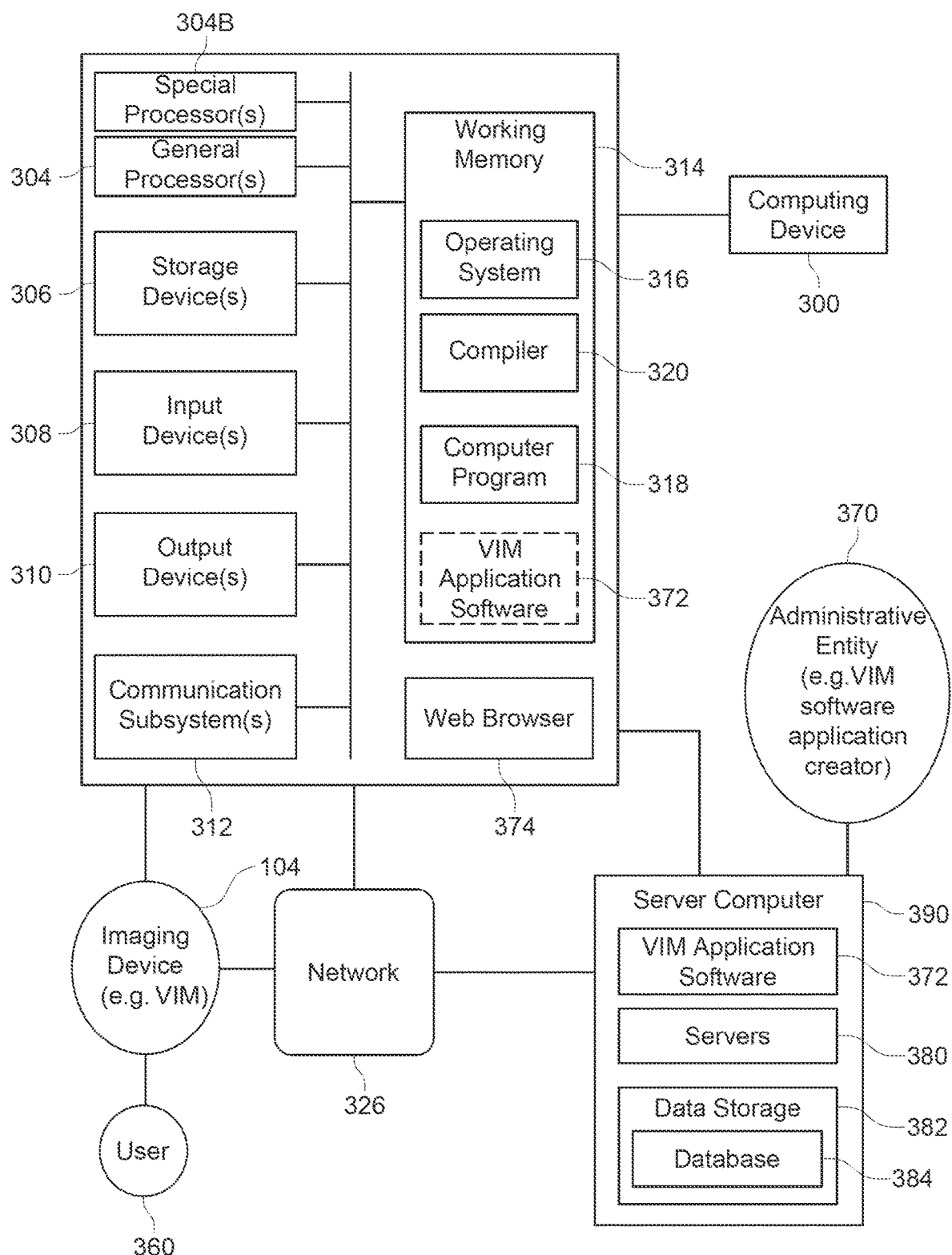
FIG. 3 illustrates an exemplary hardware and software environment used to implement one or more embodiments of the invention.

Turning to FIG. 3, FIG. 3 illustrates an exemplary system for one or more computing devices 300 and the various exemplary components that may be employed in practicing one or more non-limiting embodiments of the invention as described herein. Computing device 300 may be any type of computing device known or to be created in the future. This may include, without limitation, fixed in place computers, such as desktop computers or mobile computing devices. Mobile computing devices may include, but are not limited to, laptop computers, smartphones and mobile phones, tablets, wearable electronic computing devices such as watches or glasses, or any other type of mobile electronic, computing device. Computing device 300 may be a user/client computing device, a server computing device, or may be a database computing device. FIG. 3 is meant only to provide a generalized illustration of various components, any or all of which may be utilized as appropriate. FIG. 3, therefore, broadly illustrates how individual system elements may be implemented in a relatively separated or relatively more integrated manner.

Computing device 300 may be any type of information handling system, including, but not limited to, any type of computing device as noted above. To reiterate, this may include small handheld devices, such as handheld computer/mobile telephones or may include large mainframe systems, such as a mainframe computer. Further examples of handheld computing devices may include personal digital assistants (PDAs), personal entertainment devices, such as MP3 players, portable televisions, and compact disc players. Other examples of computing devices 300 may include, but are not limited to, laptops, notebooks, workstation computers, personal computer systems, as well as servers (e.g. servers 380).

Computing device 300 can be used by various parties described herein and may be connected on a computer network, such as computer network 326. Types of computer networks 326 that can be used to interconnect the various information handling systems may include, but are not limited to, Local Area Networks (LANs), Wireless Local Area Networks (WLANs), the Internet (e.g. World Wide Web), the Public Switched Telephone Network (PSTN), other wireless networks, and any other network topology that can be used to interconnect the information handling systems. The computing device 300 is shown comprising hardware elements that can be electrically coupled via a bus 302 (or may otherwise be in communication, as appropriate).

The hardware elements of computing device 300 may include without limitation one or more general-purpose processors 304A and/or one or more special-purpose processors 304B (such as digital signal processing chips, graphics acceleration processors, and/or the like), and generally stated as processors 304. Computing device 300 may further include one or more input devices 308, which can include without limitation one or more cameras, sensors (including inertial sensors), a mouse, a keyboard and/or the like. Further, computing device 300 may include one or more output devices 310 such as the device display. Furthermore, in some embodiments an input device 308 and an output device 310 of computing device 300 may be integrated, for example, in a touch screen or capacitive display as commonly found on mobile computing devices as well as desktop computers and laptops.

The computing device 300 may further include (and/or be in communication with) one or more non-transitory storage devices 306, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including without limitation, various file systems, database structures, and/or the like. Device storage may be used in a number of embodiments discussed herein. Further, the storage devices 306 may be non-volatile data storage devices in one or more non-limiting embodiments. Further, computing device 300 may be able to access removable nonvolatile storage devices 306 that can be shared among two or more information handling systems (e.g. computing devices) using various techniques, such as connecting the removable nonvolatile storage device 306 to a USB port or other connector of the information handling systems.

The computing device 300 might also include a communications subsystem 312, which can include without limitation a modem, a network card (wireless or wired), an infrared communication device, a wireless communication device and/or chipset (such as a Bluetooth™ device, an 802.11 device, a WiFi device, a WiMax device, cellular communication facilities, etc.), and/or the like. The communications subsystem 312 may permit data to be exchanged with a network (e.g. such as network 326), other computer systems, and/or any other devices (e.g. imaging device such as VIM). In many embodiments, the computing device 300 will further comprise a non-transitory working memory 314, which can include a RAM or ROM device, as described above.

The computing device 300 also can comprise software elements, shown as being currently located within the working memory 314, including an operating system 316, device drivers, executable libraries, and/or other code, such as one or more computer programs 318, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer). In an aspect, then, such code and/or instructions can be used to configure and/or adapt computing device 300 to perform one or more operations in accordance with the described methods.

In one embodiment, the computing device 300 operates by the general-purpose processor 304A performing instructions defined by a computer program 318 under control of the operating system 316. The computer program 318 and/or the operating system 316 may interface with the imaging device 104 and/or other device to accept input and commands and, based on such input and commands and the instructions defined by the computer program 318 and operating system 316, to provide output and results.

Some or all of the operations performed by the computing device 300 according to the computer program 318 may be implemented in a special purpose processor 304B. In this embodiment, some or all of the computer program 318 instructions may be implemented via firmware instructions stored in a read only memory (ROM), a programable read only memory (PROM) or flash memory within the special purpose processor or in memory 314. The special purpose processor may also be hardwired through circuit design to perform some or all of the operations to implement the present invention.

The computing device 300 may also implement a compiler 320 that allows an application or computer program written in a programing language such as C, C++, Assembly, Python, Prolog, SQL, RUBY, Rails, or other language to be translated into processor 304 readable code. Alternatively, the compiler 320 may be an interpreter that executes instructions/code directly, translates source code into an intermediate representation that is executed, or that executes stored precompiled code. Application or computer program 318 accesses and manipulates data received from the one or more input devices 308, output devices 310, and stored in the memory 314 of the computing device 300 using the relationships and logic that were generated using the compiler 320.

In one or more embodiments, one or more of the processors 304 implement the learning method/system or methods of imaging or identifying abnormal tissue according to one or more embodiments of the invention.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

In one or more embodiments, computing device 300 is in communication with one or more networks, such as network 326. Network 326 may include a local area network (LAN), such as a company Intranet, a metropolitan area network (MAN), or a wide area network (WAN), such as the Internet or World Wide Web. Network 326 may be a private network, a public network, or a combination thereof. Network 326 may be any type of network known in the art, including a telecommunications network, a wireless network (including Wi-Fi), and a wireline network. Network 326 may include mobile telephone networks utilizing any protocol or protocols used to communicate among mobile digital computing devices such as GSM, GPRS, UMTS, AMPS, TDMA, or CDMA. In one or more non-limiting embodiments, different types of data may be transmitted via network 326 via different protocols. In further non-limiting other embodiments, computing device 300 may act as a standalone device or may operate as a peer machine in a peer-to-peer (or distributed) network environment.

Network 326 may further include a system of terminals, gateways, and routers. Network 326 may employ one or more cellular access technologies including but not limited to: 2nd (2G), 3rd (3G), 4th (4G), 5th (5G), LTE, Global System for Mobil communication (GSM), General Packet Radio Services (GPRS), Enhanced Data GSM Environment (EDGE), and other access technologies that may provide for broader coverage between computing devices if, for instance, they are in a remote location not accessible by other networks.

In one or more non-limiting embodiments, a computing device, such as computing device 300 may include a web browser such as web browser 374. Web browser 374 may be any type of web browser known in the art that may be used to access one or more web applications (e.g. VIM application 372) on user computing device 300 or the like. Web applications are applications that are accessible by network 326 and may be located on the Internet or World Wide Web. Web browser 374 may include a variety of hardware, software, and/or firmware generally operative to present a web application to a user via a display device 310 (e.g. touchscreen or other type of monitor or display device) on a computing device. Examples of suitable web browsers include, but are not limited to, MICROSOFT EXPLORER, MOZILLA FIREFOX, GOOGLE CHROME, and APPLE SAFARI. Web browser 374 may be previously installed by the manufacturer or company associated with the computing device 300, or alternatively, may be downloaded onto computing device 300 or any other computing device.

In one or more non-limiting embodiment, VIM application 372 may be a software program or module configured to display live images and store images received from the VIM. VIM application 372 may provide a computer-based platform or software module that allows users to view the recorded video and still images received from the VIM during a procedure, whereby a user of the imaging device 104 can view any part of the video and images. Further, VIM application 372 may be an integrated system that allows the users 360 of the imaging system shown in FIG. 3 to review a stored copy of a procedure which may include and not be limited to video and/or captured images (e.g. image 102 in FIG. 1). In one or more non-limiting embodiments, the users 360 of the imaging system shown in FIG. 3 is a healthcare professional.

In one or more non-limiting embodiments, VIM application 372 may be implemented as a web service. As known in the art, a web service may be a software module or software program that is designed to implement a set of tasks that is accessible from multiple computing devices, such as computing device 300 over a network, such as network 326. In particular, VIM application 372 may be implemented as a web service accessible using the World Wide Web as the connecting network 326, although any alternative type of network may be used. VIM application 372, when implemented as a web service, can be searched by any user using web browser 374. VIM application 372 when implemented as a web service can be searched for over the network 326 using the input devices 308 of a computing device and can also be invoked accordingly. Further, VIM application 372 when invoked as a web service would be able to provide functionality to the client or user which invokes that web service.

In one or more non-limiting embodiments, a server computer 390 may be a cloud-based type hosting system. "Cloud-based" is a term that refers to applications, services, or resources (e.g. VIM application 372) made available to users on demand via a network, such as network 326, from a cloud computing provider's server. In one non-limiting embodiment, administrative entity 370 may be the cloud computing provider and may use servers 380 to provide access to VIM application 372.

Server computer 390 may include data storage systems 382 that can provide access to stored data by applications running on computing devices (e.g. 300) that may be geographically separate from each other, provide offsite data backup and restore functionality, provide data storage to a computing device with limited storage capabilities, and/or provide storage functionality not implemented on a computing device (e.g. 300).

In one or more non-limiting embodiments, an administrative entity 370 is the provider and creator of VIM application 372. Administrative entity 370 may provide the application programming interface (e.g. VIM application 372) for use by the user 360 of the imaging device 104 and the computing device 300. Administrative entity 370 may be able to manipulate and alter VIM application 372 to affect the operation and maintenance of VIM application 372 on server(s) 380 and as stored on one or more data storage systems 382 that are part of the server computer 390. Data storage systems 382 included for storing any data associated with VIM application 372 may include one or more databases 384 that store the imaging data. Data storage systems 382, via databases 384 in some cases, may be able to store all imaging data obtained from a plurality of computing devices (e.g., 300). While administrative entity 370 is depicted as a single element communicating over network 326 and through the server computer 390, it is noted that administrative entity 370, in one or more non-limiting embodiments, may be distributed over network 326 in any number of physical locations.

In one or more non-limiting embodiments, VIM application 372 may alternatively be a downloadable software module that is capable of being stored directly on a computing device, such as computing device 300, rather than acting as a web service accessible through a computing device's web browser 374. Accordingly, any user 360 may be able to download and use VIM application 372 on computing device 300 as a computer-based application (e.g. such as computer program 318) and software module that runs using the working engines and modules on the computing device 300. In some embodiments, VIM application 372 may be preinstalled on computing device 300 or any other computing device by the manufacturer or designer or other entity.

In one non-limiting embodiment, imaging device 104 can connect either wirelessly or through a wired connection to computing device 300 and any data provide by imaging device 104 may be stored on either the working memory 314 of computing device 300 or may be stored and made accessible from the data storage systems 382 and database 384 of a remote server computer 390 that also hosts the VIM application 372.

Figure 4:
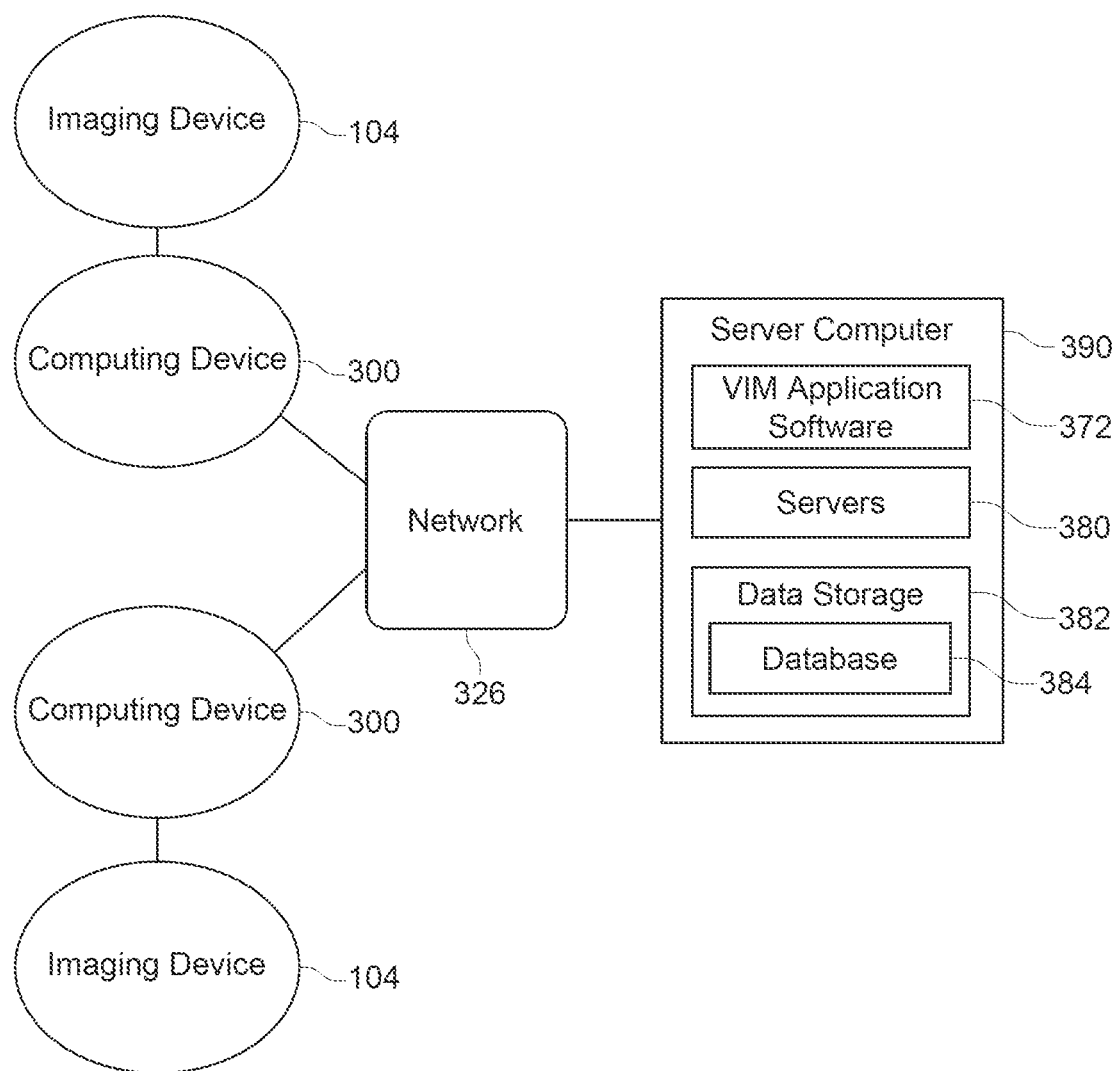
FIG. 4 schematically illustrates a typical distributed computer system, according to one or more embodiments of the invention.

Turning to FIG. 4, FIG. 4 schematically illustrates a typical distributed computing system using the network 326 to connect a plurality of computing devices 300 to server computers 390. FIG. 4 further illustrates a cloud and/or parallel computing system, according to one or more embodiments, wherein the data obtained from the images captured from a plurality of imaging devices 104 (e.g. as discussed above in FIG. 1) is shared over the network 326, so that the machine learning learns to identify one or more normal tissue and/or one or more abnormalities from the data obtained from a plurality of imaging devices 104 during endotracheal intubation (or other) procedures on a plurality of different patients/cases. Thus, the machine learning can learn from the data obtained from different procedures. The machine learning can be implemented on a plurality of computing devices 300 in the system.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or table of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

As discussed above, laryngoscope includes an optical conduit (see, FIGS. 1 and 2 at 224) which is configured to function as a conduit for the electrical wires connecting the electrical and power components in the housing (see, FIG. 1 at 202) to the light source at the distal tip of the blade (see, FIGS. 1 and 2). The invention in the present disclosure may be achieved in at least two ways. One iteration would involve replacing the existing optical conduit 224, shown in FIGS. 1 and 2, with a differently configured optical conduit which may be provided as a replacement kit and discussed below. Another iteration would involve manufacturing a completely new laryngoscope device 200 which incorporates the video imaging system and its functional elements as one device.

The first iteration of the present disclosure replaces the existing optical conduit and the components inside the housing. In this iteration, all the functional electronic elements associated with the video imaging system may be housed inside the laryngoscope handle 212 with a new optical conduit (not shown) replacing the existing laryngoscope optical conduit (see, FIGS. 1 and 2 at 224) on the laryngoscope (see, FIG. 1 at laryngoscope device 200).

In more detail, the video imaging device (e.g., camera or fiberoptic element) may be positioned at a distal end of the new optical conduit. The distal tip of the new optical conduit would be positioned at the distal end of a laryngoscope blade from which the optical conduit (see, 224 in FIGS. 1 and 2) is being replaced. In a non-limiting embodiment of the first iteration, the video imaging device is comprised of a camera. The camera may be housed in the distal tip of the new optical conduit and would be electrically connected to the internal electronic components housed within the handle (see, 212 in FIG. 1). In an alternate non-limiting embodiment of the first iteration, the video imaging device would comprise of the fiberoptic element. The fiberoptic element may be housed in the distal tip of the new optical conduit and would transmit images from the tip of the new optical conduit to the electrical components contained within the laryngoscope handle for processing into digital images.

The second iteration (not shown) would comprise of a laryngoscope which would be manufactured with all the functional elements of the video imaging system, comprising a video imaging device (e.g., camera or fiber optic element) and the associated electronic components. The physical characteristics and set up would be similar to the first iteration wherein the video imaging device (e.g., camera or fiberoptic element) would be housed in a distal top of an optical conduit. The video imaging device in the optical conduit would be positioned at a distal tip of a laryngoscope blade. Similar to the first iteration, in a non-limiting embodiment wherein the video imaging device comprises of a camera, the camera may be housed in the distal tip of the optical conduit and would be electrically connected to the internal electronic components housed within the handle (see, 212 in FIG. 1). In an alternate non-limiting embodiment, a fiberoptic element would comprise the video imaging device of the video imaging system. The fiberoptic element may be housed in the distal tip of the optical conduit and would transmit images from the tip of the optical conduit to the electrical components contained within the laryngoscope handle for processing into digital images.

As discussed above, the electronic components of the video imaging system associated with the video imaging device (e.g., camera or fiberoptic element) would be housed in the laryngoscope handle (see e.g., 212 FIG. 1). The associated electronic components may comprise of a wireless transmitter for wirelessly transmitting the output of the video imaging device to a wireless receiver that is coupled to a computing device with a video display system. The video display system may be a video monitor, screen, or another device with a screen such as a smartphone, tablet, or personal computer. The video imaging system may output still images or moving images to the computing device. The electronic components may also comprise of a microprocessor and a wireless communication chipset. The microprocessor may be utilized for functions including video processing, encoding and streaming and also for still image processing and encoding. The wireless communication chipset may function with 802.11, Bluetooth®, or another wireless communication protocol capable of streaming video. The wireless communication chipset may be integrated into or with the microprocessor chip.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A scope system, the scope system comprising: a scope having a handle, a blade attached at a first end to the handle, and a detachable component that is disposable and slidingly positionable over the blade, wherein the detachable component extends from the handle to a second end of the blade, the detachable component having a camera or fiber optic element enclosed in the detachable component in a reusable housing removable from the detachable component after each use wherein a power source and a transmitter are stored in the reusable housing; and
one or more computing devices, the one or more computing devices are configured for:
displaying an image of a region associated with the scope being guided during a visual exam.

2. The scope system of claim 1, the one or more computing devices further configured for:
obtaining a set of training data from the image or patient data from a first patient.

3. The scope system of claim 2, the one or more computing devices further configured for:
receiving one or more captured images captured by the one or more cameras at a later time than the set of training data during a visual examination using the scope; and
generating, using machine learning trained using the set of training data, one or more indicators identifying one or more abnormalities in the one or more captured images.

4. The scope system of claim 2, the one or more computing devices further configured for:
obtaining a second set of training data.

5. The scope system of claim 4, the one or more computing devices further configured for:
storing the set of training data and the second set of training data in one or more databases on a cloud server and a first medical record associated with the first patient for live display and storage separate from the cloud server;
using pattern recognition to recognize correlations between the set of training data and the second set of training data;
classifying the set of training data and the second set of training data based on the pattern recognition;
determining correlations between the image with the first medical record; and
applying the correlations to one or more second images.

6. The scope system of claim 5, further comprising one or more inertial sensors.

7. The scope system of claim 5, the one or more computing devices further configured for:
providing access to the set of training data and the second set of training data in the one or more databases to one or more second computing devices.

8. The scope system of claim 1, the one or more computing devices further configured for:
using shared data or predictive modeling to identify or predict abnormal growth; and
generating one or more viewable indicators identifying one or more abnormalities and one or more normal regions.

9. A scope system, the scope system comprising: a scope having a handle, a blade that is attached to the handle at a first end of the blade, and a detachable component having a camera or fiber optic element enclosed in the detachable component, and a transmitter, the detachable component having an attaching component slidable over the blade and positionable in and through enclosure on a sidewall of the blade to fit the camera or fiber optic element along the sidewall the blade such that the camera or fiber optic element is directed toward and facing a front side of the blade; and
one or more computing devices, the one or more computing devices configured for:
transmitting captured content by the transmitter.

10. The scope system of claim 9, the one or more computing devices further configured for:
training a machine to recognize images of glottis and surrounding tissue from the captured content; and
preforming autonomous intubation in response to the training.

11. The scope system of claim 10, the one or more computing devices further configured for:
storing the captured content in one or more databases; and
processing a compiled captured content data set in combination with other correlated clinical information to provide novel medical insights into a diagnosis, treatment, and natural progression of a disease.

12. The scope system of claim 11, wherein the one or more databases are accessible by a cloud-based storage and AI platform.

13. A scope system, the scope system comprising: a scope having a handle, a blade, and one or more cameras to capture one or more images during an endotracheal intubation, a transmitter, and support vector machine that analyzes training data and recognize patterns or correlations in the training data and subsequently build a model to classify images of tissue as normal or abnormal;
an optical conduit connected to the scope wherein a detachable component is positioned on a top side along the optical conduit;
a light source at a tip of the blade wherein the optical conduit is replaceable and functions as a conduit for electrical wires connecting electrical and power components to the light source; and
an electrical component, wherein the one or more cameras are housed in the detachable component.

14. The scope system of claim 13, wherein the one or more cameras are removably connected to the scope.

15. The scope system of claim 14, wherein the one or more cameras are adjustable in relation to the scope while connected to the scope.

16. The scope system of claim 13, the scope system having one or more computing devices performing steps of:
transmitting captured content to be integrated into a medical record; and
analyzing correlations between the captured content and the medical record to identify patterns in an image associated with a particular element in the medical record.

17. The scope system of claim 16, the one or more computing devices configured for:
obtaining the training data from the captured content of a first patient;

identifying or predicting abnormal growth; and sharing captured content with one or more second computing devices for machine learning to learn from the training data to identify one or more abnormalities in a second image of a second patient.

\* \* \* \* \*